(12) United States Patent
Kilcran

(10) Patent No.: US 10,663,984 B2
(45) Date of Patent: May 26, 2020

(54) ELECTRONIC FLOWMETER WITH REGULATOR

(71) Applicant: Medtec Medical, Inc, Buffalo Grove, IL (US)

(72) Inventor: Michael D. Kilcran, Antioch, IL (US)

(73) Assignee: Medtec Medical, Inc., Buffalo Grove, IL (US)

( * ) Notice: Subject to any disclaimer, the term of this patent is extended or adjusted under 35 U.S.C. 154(b) by 0 days.

(21) Appl. No.: 15/788,234

(22) Filed: Oct. 19, 2017

(65) Prior Publication Data

US 2018/0106655 A1 Apr. 19, 2018

Related U.S. Application Data

(60) Provisional application No. 62/409,953, filed on Oct. 19, 2016.

(51) Int. Cl.
| | |
|---|---|
| *G05D 7/06* | (2006.01) |
| *F16K 37/00* | (2006.01) |
| *A61M 16/00* | (2006.01) |
| *G01F 15/00* | (2006.01) |
| *G01F 15/06* | (2006.01) |
| *G01F 15/14* | (2006.01) |
| *A61H 9/00* | (2006.01) |
| *F16K 31/02* | (2006.01) |

(52) U.S. Cl.
CPC ....... *G05D 7/0635* (2013.01); *A61M 16/0003* (2014.02); *F16K 37/005* (2013.01); *F16K 37/0083* (2013.01); *G01F 15/002* (2013.01); *G01F 15/005* (2013.01); *G01F 15/063* (2013.01); *G01F 15/14* (2013.01); *A61H 9/0078* (2013.01); *A61M 2016/003* (2013.01); *A61M 2016/0039* (2013.01); *A61M 2205/18* (2013.01); *A61M 2205/3334* (2013.01); *A61M 2205/3592* (2013.01); *A61M 2205/502* (2013.01); *A61M 2205/583* (2013.01); *F16K 31/02* (2013.01); *Y10T 137/7759* (2015.04); *Y10T 137/7761* (2015.04); *Y10T 137/8242* (2015.04); *Y10T 137/8326* (2015.04)

(58) Field of Classification Search
CPC ........... G05D 7/0635; Y10T 137/7761; Y10T 137/7759; Y10T 137/8326; Y10T 137/8242; F16K 37/005; F16K 37/0083; G01F 15/002; G01F 15/06; G01F 1/56
See application file for complete search history.

(56) References Cited

U.S. PATENT DOCUMENTS

| | | |
|---|---|---|
| 5,785,050 A | 7/1998 | Davidson et al. |
| 5,911,219 A | 6/1999 | Aylsworth et al. |

(Continued)

FOREIGN PATENT DOCUMENTS

WO 2011130367 A1 10/2011

*Primary Examiner* — Atif H Chaudry
(74) *Attorney, Agent, or Firm* — Price Heneveld LLP

(57) ABSTRACT

An electronic flowmeter includes a body defining an interior, an inlet port in communication with the interior, an outlet port in communication with the interior, and a valve selectively adjustable between open and closed positions for communication between the outlet port and the interior. A flow sensor is associated with the valve and sensing a flowrate therethrough, and a digital indicator displays the flowrate sensed by the flow sensor.

20 Claims, 4 Drawing Sheets

(56) References Cited

U.S. PATENT DOCUMENTS

| | | | |
|---|---|---|---|
| 2007/0227265 A1 | 10/2007 | Sugi et al. | |
| 2011/0118881 A1* | 5/2011 | Tai | A01G 25/162 700/282 |
| 2012/0144898 A1* | 6/2012 | Brasel | B67D 1/12 73/40.5 R |
| 2012/0186655 A1* | 7/2012 | Smirnov | G05D 7/0635 137/1 |
| 2013/0299000 A1* | 11/2013 | Gillette, II | B67D 3/0003 137/2 |
| 2015/0107507 A1 | 4/2015 | Bluemner et al. | |
| 2015/0362939 A1* | 12/2015 | Takijiri | G05F 1/66 700/297 |
| 2016/0076909 A1* | 3/2016 | Klicpera | G06Q 50/06 73/198 |

* cited by examiner

ELECTRONIC FLOWMETER WITH REGULATOR

CROSS-REFERENCE TO RELATED APPLICATIONS

This application claims priority under 35 U.S.C. 119(e) to U.S. Provisional Patent Application No. 62/409,953, filed Oct. 19, 2016, entitled "ELECTRONIC FLOWMETER WITH REGULATOR," which is herein incorporated by reference in its entirety.

FIELD OF THE INVENTION

The present disclosure relates to flowmeters that measure fluid flow, and more particularly, the present disclosure relates to flowmeters that include regulators for adjusting the flow settings of fluid through the flowmeter.

BACKGROUND OF THE INVENTION

Flowmeters that measure fluid in a gaseous state, such as oxygen, nitrogen or nitric oxide, are often used to dispense the fluid in prescribed doses for therapeutic purposes. As an example, patients requiring oxygen obtain a prescription for a certain concentration of oxygen, a certain flowrate or volume of oxygen, and a certain time period for the delivery of oxygen. The oxygen is delivered from an oxygen source, such as an oxygen concentrator, through the flowmeter, to the patient. When the oxygen is delivered from the oxygen source, it is measured by the flowmeter and adjusted by the regulator to dispense the appropriate flowrate of oxygen for delivery to the patient.

Known flowmeters are generally in fluid communication with an oxygen source and have a ball indicator for indicating the flow rate to the user. Such flowmeters may include a meter body having an inlet port, and an outlet port. Downstream of the inlet port and upstream of the outlet port is a "Thorpe" tube that houses the ball indicator. Oxygen flows into the meter body at the inlet port, through the Thorpe tube, and out the outlet port. The oxygen in the Thorpe tube elevates a ball of the ball indicator upwards against gravity. A visual comparison of the ball up with an adjacent flowtube scale within the Thorpe tube indicates the flow rate of oxygen through the flowmeter. A regulator is adjustable by the user, and is operated by a knob to alter the flow through a fluid communication channel in the flowmeter. The regulator may be a needle valve, including a needle portion that extends into the fluid communication channel adjacent the outlet. Typically, the valve shaft is threaded, and receives an internally threaded boss. By rotating an associated knob, the needle moves axially to either be inserted into, or pulled away from, the fluid communication channel, which operates to open or close the outlet. When the user adjusts the knob, the flowrate through the fluid communication channel is changed. Corresponding flowrate information is obtained by a visual inspection of the suspended ball aligned against the flowtube scale.

There are several drawbacks of flowmeters of the above description. In one example, there can be difficultly in a user to comparing the alignment of the ball against the scale. Further, when flowrate falls outside of prescribed ranges, it is incumbent on the user to visually inspect the location of the ball on the scale, to acknowledge that the ball is out of range, and to adjust the knob of the regulator until the condition is back within the prescribed range.

SUMMARY OF THE INVENTION

According to an aspect of the disclosure, an electronic flowmeter includes a body defining an interior, an inlet port in communication with the interior, an outlet port in communication with the interior, and a valve selectively adjustable between open and closed positions for communication between the outlet port and the interior. A flow sensor is associated with the valve and sensing a flowrate therethrough, and a digital indicator displays the flowrate sensed by the flow sensor.

According to another aspect of the disclosure, a flowmeter includes a body defining an interior, an inlet port and an outlet port in fluidic communication with each other through the body, an electronic regulator maintaining a predetermined flowrate of fluid between the inlet port and the outlet port, and a touch screen in communication with the electronic regulator for one of inputting or adjusting the predetermined flowrate.

According to another aspect of the disclosure, a flowmeter includes a body defining an interior, an inlet port in communication with the interior, an outlet port in communication with the interior, and a valve selectively adjustable between open and closed positions for communication between the outlet port and the interior. An electronic regulator maintains a predetermined flowrate of fluid between the inlet port and the outlet port, and a touch screen is in communication with the electronic regulator for one of inputting or adjusting the predetermined flowrate.

Further objects and advantages of the invention will be apparent from the drawings and the following detailed description of preferred embodiments.

These and other features, advantages, and objects of the present invention will be further understood and appreciated by those skilled in the art by reference to the following specification, claims, and appended drawings.

DETAILED DESCRIPTION OF THE PREFERRED EMBODIMENTS

Figure 1:
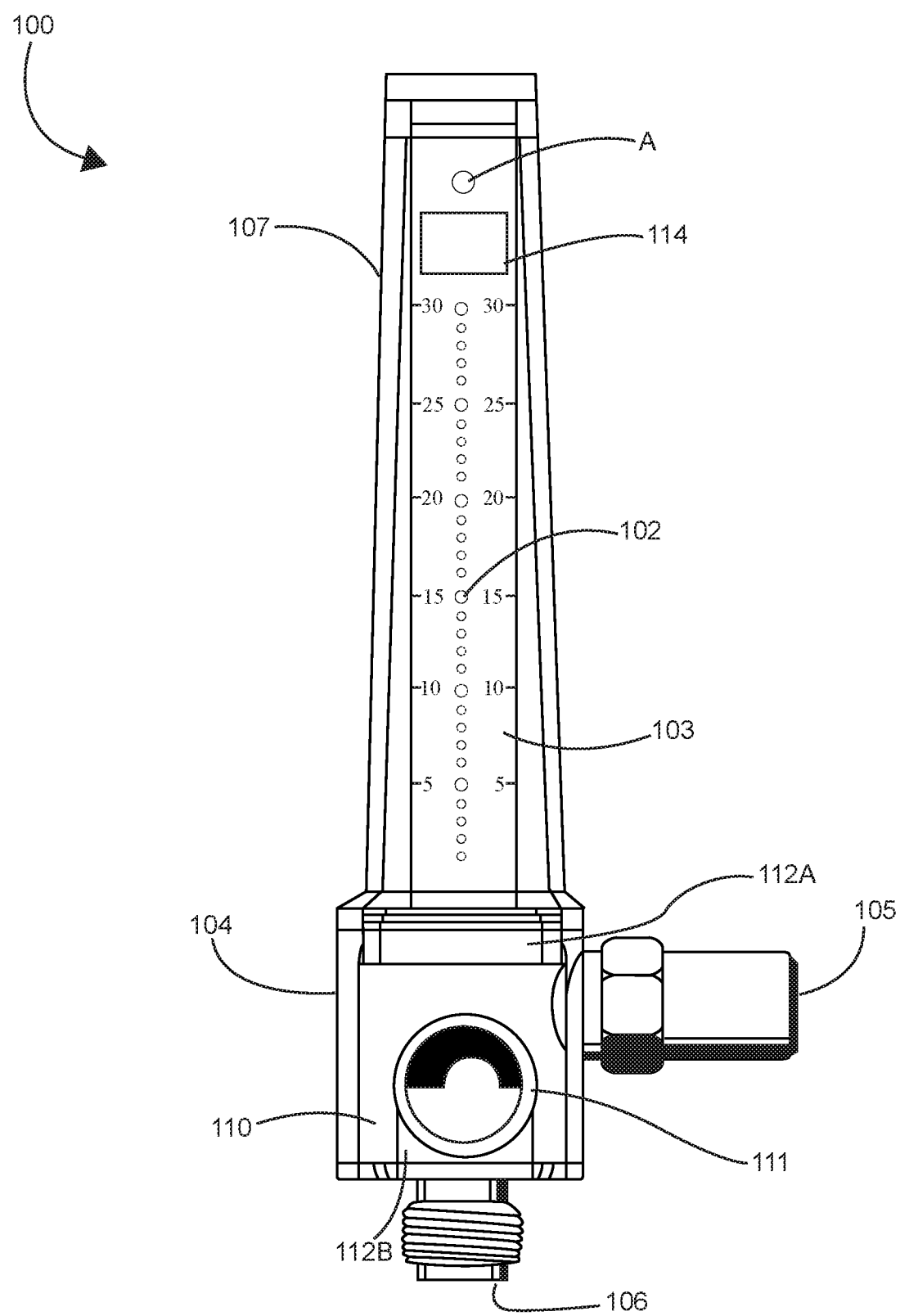
FIG. 1 is a flowmeter having a digital display according to an aspect of the disclosure.

Referring now to FIG. 1, a first embodiment of a flowmeter 100 is configured to be in fluid communication with an oxygen source 2 (see FIG. 1), and as will be described below, has a digital indicator 103, preferably in the form of an LED (light-emitting diode) display, that provides the user with the flow rate of the oxygen through the flowmeter. The flowmeter 100 includes a meter body 104 and a tube 107 that extends from the meter body. As can be seen in FIG. 1, the digital indicator 103 may extend away from the meter body 104 along a portion of the tube 107. The meter body 104 has an inlet port 105 and outlet port 106. As can be seen in FIG. 1, the outlet port 106 may be positioned generally perpendicular to the inlet port 105. Additionally, the outlet port 106 may be positioned in axial alignment with the tube 107.

Oxygen flows into the meter body 104 at the inlet port 105, through a first fluid communication channel 112A, through the tube 107, through a second fluid communication channel 112B, and out of the outlet port 106.

In the first example of FIG. 1, a regulator 110 is a mechanical valve that is operated by a knob 111 to alter the flow through a fluid communication channel 112B in the flowmeter 100, as is known in the prior art. As can be seen in FIG. 1, the regulator 110, or valve, may be disposed within the meter body 104 between the inlet port 105 and the outlet port 106. When the user controls the flow of oxygen, the user adjusts the knob 111, which restricts or opens the fluid communication channel 112B, which changes the flowrate through the fluid communication channel.

Figure 3:
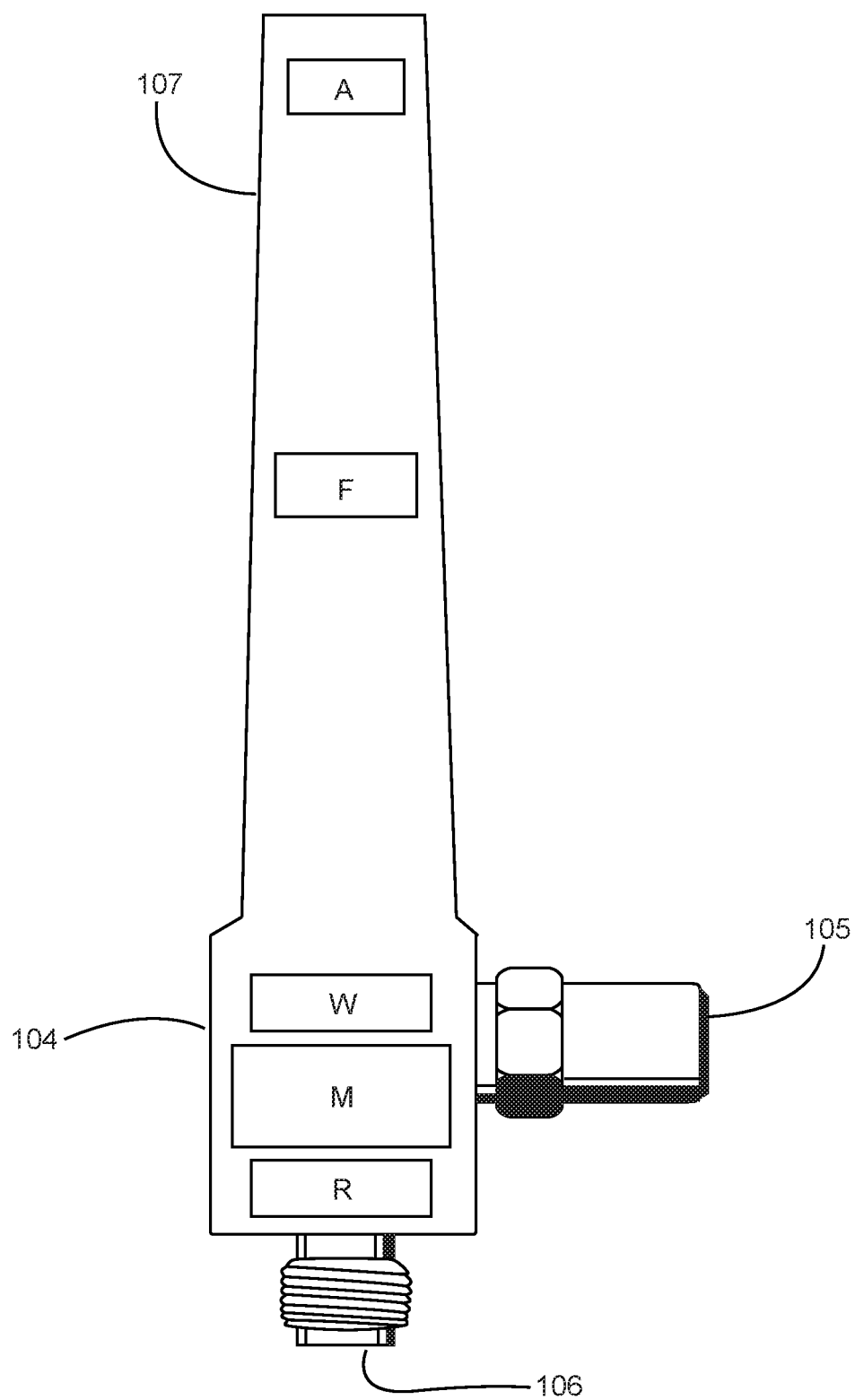
FIG. 3 is a schematic of sensors and a microprocessor associated with a flowmeter according to either of the flowmeters of FIGS. 1 and 2.
Figure 4:
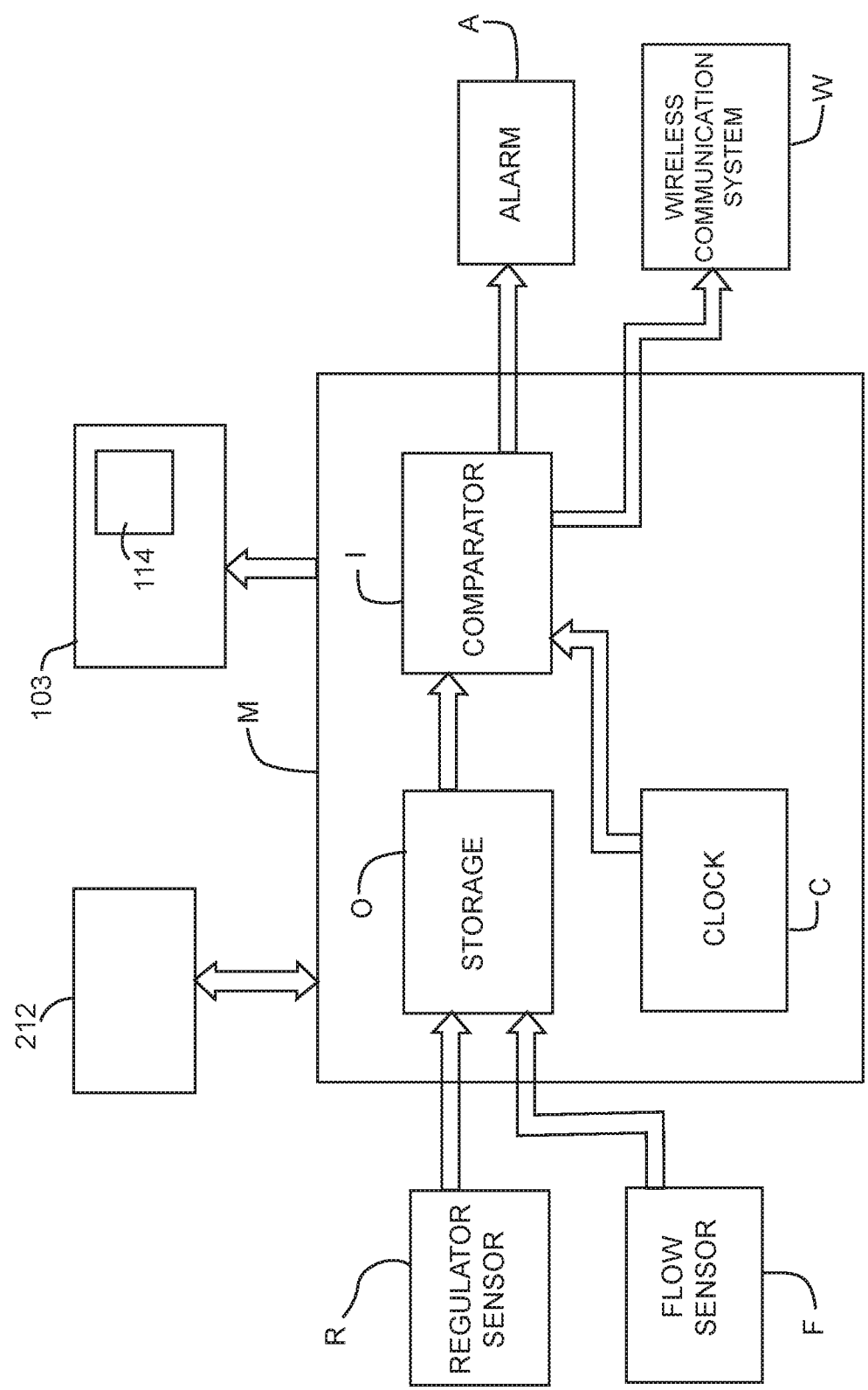
FIG. 4 is a block diagram of the communication between components of the flowmeters and their connection to the microprocessor.

Referring to FIGS. 1, 3 and 4, an electronic flow sensor F, such as those commercially available from Proportion-air or Koge Micro Tech Co, is located in the tube 107 and senses the flowrate of oxygen through the tube. The electronic flow sensor F communicates the flowrate value to a microprocessor M, which displays the flowrate value on the LED display 103. Changes in flowrate are tracked in real-time with information provided by the electronic flow sensor F, and the flowrate value is obtained by a visual inspection by the user of the LED display 103.

Preferably, the LED display 103 includes a plurality of LED lights 102 in a column that is associated with indicia for measurement of fluids, for example liters per minute. In the preferred embodiment, the indicia ranges between 0 and 30 liters/minute. In one example, when the flowrate is 15 liters/minute, the LEDs associated with values 0 through 15 liters/minute are illuminated. Alternately, only the LED associated with the numerical value of 15 liters/minute is illuminated. Further, a digital display of the numeric value "15" may be displayed, for example on a LCD (liquid crystal display) screen 114.

Figure 2:
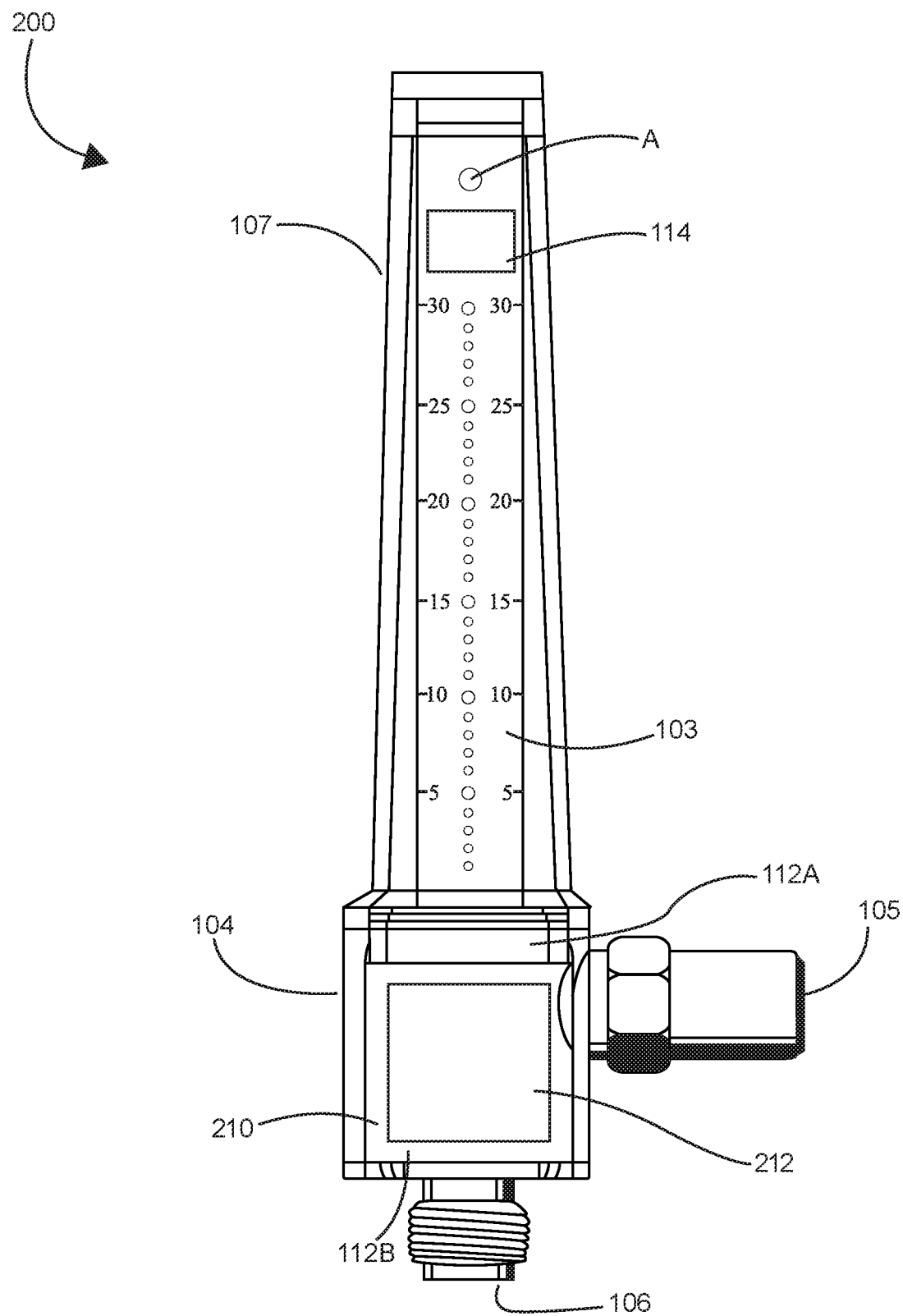
FIG. 2 is a flowmeter having a digital input according to a further aspect of the disclosure.

In the second example of FIG. 2, a flowmeter 200 is substantially the same as the first example of flowmeter 100 with a digital indicator 103 such as an LED display, except that the flowmeter 200 includes a regulator 210 that is an electronic valve or solenoid, for example those that are commercially available from Koge Micro Tch Co. or MKS Instruments, are appropriate for use in an oxygen environment. The regulator 210 may be operated by either a mechanical input device, such as a knob (which may be similar to knob 111 shown in FIG. 1), or alternatively, may be operated by a touch screen 212 or other input device (such as a rocker switch, buttons, or the like). It is contemplated that the touch screen 212 may be backlit, and that the touch screen maybe be programmed to turn off within a predetermined amount of time, for example after five minutes of the last user input.

Referring now to FIGS. 2-4, with the electronic regulator 210, the setting of the regulator can be monitored with a regulator sensor R that monitors the setting of the flowmeter 200 and communicates the setting to the microprocessor M. In this way, the electronic regulator 210 can be automatically operated based on feedback from the regulator sensor R. The setting of the flowmeter 200 is displayed at the touch screen 212 and/or at the LED display 103 and/or LCD screen 114. It is contemplated that only one display is needed to indicate all settings and alarms associated with the flowmeter 200. The regulator sensor R may be an infra-red emitter and photodetector which generates an electrical signal depending on the distance between the components of the electronic valve as they open or close off the fluid communication channel 112B. It is contemplated that other types of regulator sensors R may be used.

The microprocessor M of flowmeter 100, 200 is provided with a memory storage O to store prescription data and/or the readings from the flow sensor F and/or the readings from the regulator sensor R. The memory storage O, a clock C and a comparator I allow the microprocessor M to be programmed to operate the flowmeter 100, 200 under prescribed ranges of flow for prescribed durations of time. In one embodiment, the microprocessor M may be programmed to automatically operate at differing flow levels over time, and may include a range of preset flows or a range dictated by caregiver. The microprocessor M may automatically shut-off the flowmeter 100, 200 when flow levels exceed or drop below a certain range, or alternatively, may hold levels at the range outer limits.

The microprocessor M also allows for storage of historical data and calibration between the flow sensor F and the regulator sensor R. While the microprocessor M is preferably contained within the flowmeter 100, 200, it is contemplated that the microprocessor can be located remotely.

The flowmeter 100, 200 is preferably provided with an alarm A that is responsive to signals generated by the flowrate sensor F and/or the regulator sensor R. The alarm A may be an audible alarm and/or a visual alarm, such as an LED on the flowmeter. Conditions in which the alarm A might be initiated are when the flow level is out of a prescribed range, or when there is no flow. For example, when the oxygen levels are not within prescribed range as stored in the memory storage O of the microprocessor M, or not within a prescribed time-period as compared at a comparator I with a clock C, an audible alarm and/or visual indicator is initiated. When the condition is corrected and levels return to within the prescribed parameters, the alarm A will automatically cease operation. It is contemplated that the alarm A can be located either or both upstream or downstream of the flowmeter 100, 200 for indicating low volume and/or low pressure conditions.

A wireless communication system W connects the flowmeter 100, 200 to broadcast the flow rate in real time, and in particular, any alarm conditions, to remote locations. Examples of such remote locations include the nurses' station in a hospital setting, as well as to home care providers. The wireless communication system W can be integrated with an existing hospital alarm system, and with health records systems. The wireless communication system W can also be used to communicate with personal devices of health care providers, such as cell phones, pagers, tablets and other personal computers. The wireless communication system W may be a Wi-Fi or BLUETOOTH® system, however other systems are contemplated.

The flowmeter 110, 210 can be used in a "DVT" mode in conjunction with a deep vein thrombosis garment, obviating the need for a separate pump for DVT compression therapy. The flowmeter 110, 210 monitors and regulates a positive pressure to a DVT garment at a range of about 40 mm/HG to about 150 mm/HG, and preferable is controlled by the user at the touch screen input device 212. It is contemplated that as part of the DVT mode, intermittent inflation and deflation of the DVT garment is controlled by the flowmeter 110, 210. For example, the flowmeter 110, 210 may control the inflation of the DVT garment over a period of time, for example 1-minute, and then may hold or control the deflation of the DVT garment over a subsequent period of time, for example 1-minute. It is contemplated that the flowmeter 110, 210 may control one or more DVT garments on one or more patient limbs for varying periods of time.

It is contemplated that the flowmeter 110, 210 may be powered by mains power, battery power, solar power, and/or an in-line turbine, among other power sources.

With both embodiments of flowmeter 100, 200, it is contemplated that the upper threshold of flowrate value that is measurable by the flowmeter is preferably around 30 liters/minute, although other values are contemplated.

With the flowmeters 100, 200, it is preferred that all exterior surfaces are treated with an anti-microbial agent, such as MicrobeCare™, quaternary ammonium antimicrobials, heavy metals such as silver and copper, poisons such as chlorhexidine (CHG), biguanides and Triclosan.

Since modifications within the spirit and scope of the invention may readily be effected by persons skilled within the art, it is to be understood that this invention is not limited to the particular embodiments described by way of example hereinabove. In the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

REFERENCE NUMBERS IN THE DRAWINGS

| | |
|---|---|
| 100, 200 | Flowmeter |
| 102 | LED lights |
| 103 | Digital Indicator |
| 104 | Meter Body |
| 105 | Inlet Port |
| 106 | Outlet Port |
| 107 | Tube |
| 110, 210 | Regulator |
| 111 | Knob |
| 112A | First Fluid Communication Channel |
| 112B | Second Fluid Communication Channel |
| 114 | LCD Screen |
| 200 | Flowmeter |
| 210 | Electronic Regulator |
| 212 | Touch Screen |
| F | Electronic Sensor of Flowrate |
| M | Microprocessor |
| R | Regulator Sensor |
| O | Storage |
| C | Clock |
| I | Comparator |
| A | Alarm |
| W | Wireless Communication System |

The invention claimed is:

1. An electronic flowmeter for controlling the therapeutic delivery of a gaseous fluid to a patient, comprising:
   a body defining an interior;
   a tube mounted to and extending from the body;
   an inlet port in fluid communication with the interior;
   an outlet port in fluid communication with the interior and positioned generally perpendicular to the inlet port and in axial alignment with the tube;
   a valve selectively adjustable between open and closed positions for fluid communication between the outlet port and the interior, the valve disposed within the body between the inlet port and the outlet port;
   a flow sensor at least partially located within the tube and in fluid communication with the valve for sensing a flowrate of the gaseous fluid therethrough; and
   a digital indicator extending away from the body along a portion the tube, in communication with the flow sensor, and displaying the flowrate sensed by the flow sensor.

2. The electronic flowmeter of claim 1, wherein the digital indicator includes a plurality of LEDs sequentially illuminating proportionally with an increase in the flowrate sensed by the flow sensor.

3. The electronic flowmeter of claim 1, wherein the digital indicator includes an LCD screen displaying a digital indication of the flowrate sensed by the flow sensor.

4. The electronic flowmeter of claim 1, further including a microprocessor in electronic communication with the flow sensor and the display, the microprocessor receiving a flowrate signal from the flow sensor and outputting a corresponding control signal to the digital indicator.

5. The electronic flowmeter of claim 4, wherein:
   the valve is an electromechanical valve; and
   the microprocessor is in electronic communication with the valve to control adjustment of the valve between the open and closed positions.

6. The electronic flowmeter of claim 5, further including a regulator sensor determining a position of the valve between the open and closed positions, the microprocessor being in electronic communication with the regulator sensor to monitor the position thereof.

7. The electronic flowmeter of claim 5, wherein the microprocessor is further in communication with the flow sensor and implements a feedback control scheme to control adjustment of the valve to achieve a predetermined flowrate, as determined by the flow sensor output.

8. The electronic flowmeter of claim 7, further including an input device in communication with the microprocessor for user input of the predetermined flowrate.

9. The electronic flowmeter of claim 4, further including an output device in communication with the microprocessor, the microprocessor controlling the output device to output an alarm when the flowrate is outside of a predetermined range.

10. A flowmeter for controlling the therapeutic delivery of a gaseous fluid to a patient, comprising:
    a body defining an interior;
    a tube mounted to and extending from the body and in fluid communication with the interior;
    an inlet port and an outlet port in fluid communication with each other through the body, wherein the outlet port is positioned generally perpendicular to the inlet port and in axial alignment with the tube;
    an electronic regulator maintaining a predetermined flowrate of the gaseous fluid between the inlet port and the outlet port; and
    a touch screen extending away from the body along a portion of the tube and in communication with the electronic regulator for one of inputting or adjusting the predetermined flowrate.

11. The flowmeter of claim 10, further including a regulator sensor that senses a position of the electronic regulator within a range of positions between a fully-opened position and a fully-closed position.

12. The flowmeter of claim 11, further including a microprocessor in electronic communication with the regulator sensor and the electronic regulator, the microprocessor receiving a position signal from the regulator sensor indicating the position of the electronic regulator.

13. The flowmeter of claim 12, wherein the microprocessor implements a feedback scheme to control the position of the electronic regulator using the position signal to achieve the predetermined flowrate.

14. The flowmeter of claim 11, wherein the regulator sensor further senses at least one of an oxygen concentration within or a flowrate of the gaseous fluid through the electronic regulator, the flowmeter further including:
an output device in communication with the microprocessor, the microprocessor controlling the output device to output an alarm when the one of the oxygen concentration or the flowrate is outside of a predetermined range.

15. The flowmeter of claim 10, wherein the electronic regulator includes one of an electronic valve or a solenoid.

16. The flowmeter of claim 10, further including a digital indicator displaying the predetermined flowrate.

17. The flowmeter of claim 16, wherein the digital indicator is included in the touchscreen.

18. A flowmeter, comprising:
a body defining an interior;
a tube mounted to and extending from the body and in fluid communication with the interior;
an inlet port in fluid communication with the interior;
an outlet port in fluid communication with the interior and positioned generally perpendicular to the inlet port and in axial alignment with the tube;
a valve selectively adjustable between open and closed positions for communication between the outlet port and the interior;
an electronic regulator maintaining a predetermined flowrate of fluid between the inlet port and the outlet port;
a flow sensor at least partially located within the tube and sensing a flowrate of fluid between the inlet port and the outlet port; and
a touch screen extending away from the body along a portion of the tube and in communication with the electronic regulator for one of inputting or adjusting the predetermined flowrate.

19. The flowmeter of claim 18, wherein the touchscreen includes a digital indicator displaying the flowrate sensed by the flow sensor.

20. The flowmeter of claim 18, wherein the flowmeter is treated with an antimicrobial agent over an entire exterior thereof.

\* \* \* \* \*